United States Patent
Rabbani et al.

(10) Patent No.: US 11,181,528 B2
(45) Date of Patent: *Nov. 23, 2021

(54) ASSAYS FOR DETECTING MODIFIED COMPOUNDS

(71) Applicant: Enzo Life Sciences, Inc., Farmingdale, NY (US)

(72) Inventors: Elazar Rabbani, New York, NY (US); Jannis G. Stavrianopoulos, Bay Shore, NY (US); Joshua Rabbani, New York, NY (US); Praveen Pande, Holbrook, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 113 days.

This patent is subject to a terminal disclaimer.

(21) Appl. No.: 16/225,669

(22) Filed: Dec. 19, 2018

(65) Prior Publication Data

US 2019/0162733 A1 May 30, 2019

Related U.S. Application Data

(60) Continuation of application No. 15/195,343, filed on Jun. 28, 2016, now abandoned, which is a continuation of application No. 14/296,756, filed on Jun. 5, 2014, now Pat. No. 9,404,143, which is a division of application No. 12/806,950, filed on Aug. 24, 2010, now Pat. No. 8,778,614.

(51) Int. Cl.
  *G01N 33/68* (2006.01)
  *G01N 33/92* (2006.01)
  *C12Q 1/48* (2006.01)

(52) U.S. Cl.
  CPC ......... *G01N 33/6803* (2013.01); *C12Q 1/485* (2013.01); *G01N 33/92* (2013.01); *C12Y 207/01091* (2013.01); *C12Y 207/11001* (2013.01); *G01N 2405/08* (2013.01); *G01N 2410/00* (2013.01); *G01N 2440/14* (2013.01); *G01N 2440/30* (2013.01)

(58) Field of Classification Search
  CPC ............... G01N 33/92; G01N 2410/00; G01N 2405/08; C12Y 207/01091
  See application file for complete search history.

(56) References Cited

U.S. PATENT DOCUMENTS

| 7,056,683 B2 | 6/2006 | Ting | |
| 2005/0164338 A1* | 7/2005 | Simala-Grant | C12P 21/005 435/68.1 |
| 2006/0073542 A1* | 4/2006 | Bayer | C12N 9/1051 435/68.1 |
| 2007/0264667 A1 | 11/2007 | Gellibolian et al. | |

OTHER PUBLICATIONS

Bandhuvula et al. (J. Lipid Research 2007 48:2769-2778 ("A Rapid Fluorescence Assay for Sphingosine-1-phosphate Lyase Enzymatic Activities") (Year: 2007).*
McCauley et al., "IQtm Technology: Development of a Universal, Homogeneous Method for High-Throughput Screening of Kinase and Phosphatase Activity," *JALA: Journal of the Association for Laboratory Automation*, vol. 8, issue: 2, pp. 36-40 (2003).
Ruse et al., "Motif-Specific Sampling of Phosphoproteomes," *Journal of Proteome Research*, vol. 7, pp. 2140-2150 (2008).
Bailey et al., "MS-qFRET: A quantum dot-based method for analysis of DNA methylation," *Genome Research*, vol. 19, pp. 1455-1461 (2009).
Brustad et al., "A General and Efficient Method for the Site-Specific Dual-Labeling or Proteins for Single Molecule Flourescence Resonance Energy Transfer," *Journal of the American Chemical Society*, vol. 130, pp. 17664-17665 (2009).
Jager et al., "Site-specific labeling of proteins for single-molecule FRET by combining chemical and enzymatic modification," *Protein Science*, vol. 15, pp. 640-646 (2006).
Rideout et al., "Design and synthesis of fluorescent substrates for human tyrosyl-DNA phosphodiesterase I," Nucleic Acids Research, vol. 32, No. 15, pp. 4657-4664 (2004).
Roy et al., "A Practical Guide to Single Molecule FRET," *Nat Methods*, vol. 5, No. 6, pp. 507-516 (2008).

* cited by examiner

*Primary Examiner* — Changhwa J Cheu
(74) *Attorney, Agent, or Firm* — David Lansky, Esq.

(57) ABSTRACT

Provided are methods and compositions which are useful for separating, isolating, detecting, and quantifying compounds of interest which have been modified chemically, enzymatically or catalytically from other compounds which have not been so modified. The modifications may take the form of functional groups which are gained, lost or retained by the compounds of interest.

4 Claims, 11 Drawing Sheets

Specification includes a Sequence Listing.

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide

<400> SEQUENCE: 1

Gly Arg Pro Arg Thr Ser Ser Phe Ala Glu Gly
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 5-carboxyfluorescein label
<220> FEATURE:
<221> NAME/KEY: MOD_RES
<222> LOCATION: (11)..(11)
<223> OTHER INFORMATION: sulfated tyrosine

<400> SEQUENCE: 2

Gly Pro Trp Leu Glu Glu Glu Glu Ala Tyr Gly Trp Met Asp Phe
1               5                   10                  15
```

ASSAYS FOR DETECTING MODIFIED COMPOUNDS

CROSS-REFERENCE TO RELATED APPLICATIONS

This application is a continuation of U.S. application Ser. No. 15/195,343 filed Jun. 28, 2016, which is a continuation of U.S. application Ser. No. 14/296,756 filed Jun. 5, 2014 (now U.S. Pat. No. 9,404,143), which is a division of U.S. application Ser. No. 12/806,950 filed Aug. 24, 2010 (now U.S. Pat. No. 8,778,614), each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 19, 2018, is named ENZ-92-D1-CON-CON-SL.txt and is 1,030 bytes in size.

FIELD OF THE INVENTION

This invention relates to methods for identifying compounds of interest that gain, retain or lose functional groups. More specifically, methods are provided to isolate, detect, identify and quantify compounds that are modified by the addition or loss of functional groups.

BACKGROUND OF THE INVENTION

Biological compounds are often modified enzymatically or chemically to add or lose a functional group. These functional groups can alter the biological function of the compound significantly. An illustration of one such biochemical modification is the kinase-mediated conversion of sphingosine to sphingosine-1-phosphate, a cellular metabolite which has important signaling functions.

Several methods have been used to detect products which have been modified or converted through enzymatic processes to gain or lose a functional group. These include the use of radioisotopes, for example $^{32}P$ and $^{35}S$. As an example, the latter compound is used to detect sulfotransferase activity, where $^{35}S$-adenosine 3'-phosphate 5'-phosphosulfate (PAPS) is utilized to identify the addition of a sulfate to hydroxyl or amine moieties on a variety of xenobiotics and endogenous substrates by sulfotransferases (Weinshilboum et al., FASEB J. 11:3-14, 1997).

Affinity matrices, thin layer and column chromatography, mass spectroscopy analysis and gel electrophoresis are also used to separate compounds having various functional groups from compounds lacking such groups. Some affinity schemes rely on the recognition of new functional groups or charged groups on the biological compounds as immunological epitopes. An example is antibodies that bind to sulfonated epitopes of sclerostin, as described in U.S. patent application Ser. No. 12/802,447. Immunoprecipitation is also commonly used to detect methylated DNA. See, e.g., Thu et al., J Cell Physiol. 222:522-31 (2010). Additionally, several products are marketed that depend on the creation of new immunological epitopes for detecting modifications in biomolecules. See, for example, DELFIA®, LANCE® and AlphaScreen® assays (PerkinElmer, Inc.), IMAP® (Molecular Devices, Inc. and IQ assay and LightSpeed™ (QTL Biosystems).

Due to the importance of phosphorylation in numerous biological systems, and in particular signal transduction systems, a number of assays have been developed to detect kinase activity using fluorescent signaling moieties. See, e.g. Coffin et al., Anal. Biochem. 278:206-212 (2000); Li et al., Anal. Biochem. 384:56-67 (2009); Sun et al., Anal. Chem. 77:2043-2049 (2005); Kupcho et al., Anal. Biochem. 317: 210-217 (2003); U.S. Pat. Nos. 4,565,790; 4,808,541; 5,527,684; 6,251,581; 6,287,774; 6,743,640; 6,996,194; 7,122,383; 7,250,517; 7,262,282; 7,432,070; 7,445,894; 7,582,461; and 7,632,651, and U.S. Patent Publications 2004/0166515; 2005/0202565; 2005/0227294; and 2008/0318255. Several such kinase assays utilize Förster resonance energy transfer ("FRET") interactions to identify the phosphorylated compounds. See, e.g., Ohuchi et al., Analyst 125:1905-1907 (2000); Zhang et al., Proc. Natl. Acad. Sci. USA 98:14997-15002 (2001); Ting et al., Proc. Natl. Acad. Sci. USA 98:15003-15008; Kurokawa et al., J. Biol. Chem. 276:31305-31310 (2001); Violin et al., J. Cell Biol. 161:899-909 (2003); Hofmann et al., Bioorg. Med. Chem. Lett. 11:3091-3094 (2001); Nagai et al., Nat. Biotech. 18:313-316 (2000); Sato et al., Nat. Biotech. 20:287-294 (2002); Li et al., Anal. Bioanal. Chem. 390:2049-2057 (2008); Uri et al., Biochim. Biophys. Acta 1804:541-546 (2010); Rinisland et al., Proc. Natl. Acad. Sci. USA 101: 15295-15300 (2004); Rinisland et al., BMC Biotechnology 5:16 (2005); Rinisland et al., Assay Drug Dev. Technol. 2:183-92; European Patent Application EP1748079; LanthaScreen™, Life Technologies, Carlsbad Calif. Reviews of kinase assay technologies are provided in Ishida et al., J. Pharmacol. Sci. 103:5-11 (2007); Olive, Expert Rev. Proteomics 1:327-241 (2004); Jia et al., Curr. Drug Discov. Technol. 5:59-69 (2008); Vogel et al., Expert Opin. Drug Discov. 3:115-128 (2008); Zaman, Combinatorial Chem. High Throughput Screen. 6:313-320 (2003); Ahsen and Bomer Chem. Bio. Chem. 6:481-490 (2005); Schmidt et al., J. Chromatog. B 849:154-162 (2007); and Jia, Expert Opin. Drug Discov. 3:1461-1474 (2008).

The present invention provides two alternative approaches to the non-radioactive detection of compounds modified with functional groups. One approach utilizes physicochemical differences between the unmodified and modified compounds to separate the two compounds. The other approach uses dyes that comprise an energy transfer pair, where the configuration of the dyes differs between a compound with a functional group and the same compound without a functional group. In that approach, the configuration that comprises a charged functional group, but not the configuration with an uncharged moiety, causes an energy transfer interaction between the dyes. While currently available technologies for detecting compounds modified with functional groups are generally directed to the detection of only a single functional group (e.g., phosphate groups), both approaches disclosed herein provide advantages in that they are rapid, simple, and quantitative, and can be used with various types of compounds (e.g., small molecules, lipids and peptides) and many different functional groups.

SUMMARY OF THE INVENTION

This invention provides assays and compositions for separating, identifying, and quantifying compounds having functional groups.

In some embodiments, a method is provided for isolating a compound which has gained at least one functional group. The method comprises (a) providing: (i) a compound which can gain a functional group, the compound comprising at least one non-radioactive signaling moiety; (ii) a chemical, enzymatic or catalytic source of the functional group which can be gained by the compound; and (iii) means to separate the compound which has gained the functional group from the compound which has not gained the functional group; (b) forming a mixture comprising the compound and the source of the functional group, and incubating the mixture under conditions suitable for the compound to gain the functional group; and (c) separating and thereby isolating any compound which has gained the functional group from any compound which has not gained the functional group.

In other embodiments, a method is provided for isolating a compound which has lost at least one functional group. The method comprises (a) providing: (i) a compound comprising a functional group and at least one non-radioactive signaling moiety; (ii) a chemical, enzymatic or catalytic source which can remove the functional group from the compound; and (iii) means for separating the compound which has lost the functional group from the compound which has not lost the functional group; (b) forming a mixture comprising the compound and the chemical, enzymatic or catalytic source and incubating the mixture under conditions suitable for the compound to lose the functional group; and (c) separating and thereby isolating any compound which has lost the functional group from any compound which has not lost the functional group.

Also provided is a method for determining the addition of a charged functional group to an uncharged moiety on a compound. The method comprises (a) providing: (i) the compound without the functional group, wherein the compound further comprises one member of an energy transfer pair; (ii) a second member of the energy transfer pair, having a charge opposite to the charge of the functional group; and (iii) a chemical, enzymatic or catalytic source of the functional group capable of adding the functional group to the compound; (b) forming a mixture comprising the compound without the functional group, the second member of the energy transfer pair, and the source of the functional group and incubating the mixture under conditions suitable for the compound to add the functional group; and (c) detecting a FRET interaction between the members of the energy transfer pair, wherein the presence of the FRET interaction is indicative of the addition of the functional group to the compound.

In additional embodiments, a method is provided for determining the addition of an uncharged functional group to a charged moiety on a compound. The method comprises (a) providing (i) the compound without the functional group, wherein the compound further comprises one member of an energy transfer pair; (ii) a second member of the energy transfer pair, having a charge opposite to the charge of the moiety; and (iii) a chemical, enzymatic or catalytic source of the functional group capable of adding the functional group to the charged moiety; (b) forming a mixture of the compound without the functional group and the source of the functional group and incubating the mixture under conditions suitable for the compound to add the functional group to the charged moiety; (c) adding the second member of the energy transfer pair to the mixture of step (b); and (d) evaluating the energy transfer pair to determine the degree to which a FRET interaction occurs, wherein the addition of the functional group to the charged moiety causes a reduction in the FRET interaction.

Further provided is a method for determining the removal of a charged functional group from an uncharged moiety on a compound. The method comprises (a) providing: (i) the compound with the functional group, wherein the compound further comprises one member of an energy transfer pair; (ii) a second member of the energy transfer pair, having a charge opposite to the charge of the functional group; and (iii) a means to remove the functional group from the uncharged moiety; (b) forming a mixture of the compound with the functional group and the means to remove the functional group and incubating the mixture under conditions suitable for the functional group to be removed from the compound; (c) adding the second member of the energy transfer pair to the mixture of step (b); and (d) determining whether a FRET interaction is occurring between the members of the energy transfer pair, wherein the absence of a FRET interaction indicates that the charged functional group has been removed from the uncharged moiety by the means to remove the functional group.

Additionally, a method is provided for determining the removal of an uncharged functional group from a charged moiety on a compound. The method comprises (a) providing: (i) the compound with the functional group, wherein the compound further comprises one member of an energy transfer pair; (ii) a second member of the energy transfer pair, having a charge opposite to the charged moiety; and (iii) a means to remove the functional group from the charged moiety; (b) forming a mixture comprising the compound with the functional group, the second member of the energy transfer pair, and the means to remove the functional group from the charged moiety and incubating the mixture under conditions suitable for the functional group to be removed from the compound; (c) determining whether a FRET interaction is occurring between the members of the energy transfer pair, wherein the presence of a FRET interaction indicates that the uncharged functional group has been removed from the charged moiety by the means to remove the functional group.

In further embodiments, a reagent is provided for determining the presence of an enzyme that adds or removes a charged functional group to an uncharged moiety on a substrate. The reagent comprises the substrate to which a first member and a second member of an energy transfer pair are covalently bound at a distance such that a FRET interaction does not occur unless the charged functional group is present, wherein the second member of the energy transfer pair has a charge opposite to the charge of the functional group, and wherein the presence of the charged functional group to the substrate causes noncovalent binding of the second member of the energy transfer pair to the functional group, bringing the first member and the second member of the energy transfer pair close enough so that a FRET interaction occurs.

Additionally, a reagent is provided for determining the presence of an enzyme that adds or removes an uncharged functional group to a charged moiety on a substrate. The reagent comprises the substrate to which a first member and a second member of an energy transfer pair are covalently bound at a distance such that a FRET interaction does not occur unless the uncharged functional group is absent, wherein the second member of the energy transfer pair has a charge opposite to the charge of the moiety, and wherein the absence of the uncharged functional group causes noncovalent binding of the second member of the energy transfer pair to the charged moiety, bringing the first member and the second member of the energy transfer pair close enough so that a FRET interaction occurs.

BRIEF DESCRIPTION OF THE DRAWINGS

FIG. 1A illustrates the energy transfer pair in an intramolecular arrangement on the peptide; FIG. 1B shows the energy transfer pair in an intermolecular arrangement; and FIG. 1C shows the use of a chelator on energy transfer dye F2 and metal ion to cause binding of a functional group to F2 in an intermolecular arrangement.

DETAILED DESCRIPTION OF THE INVENTION

Definitions

Figure 1A:
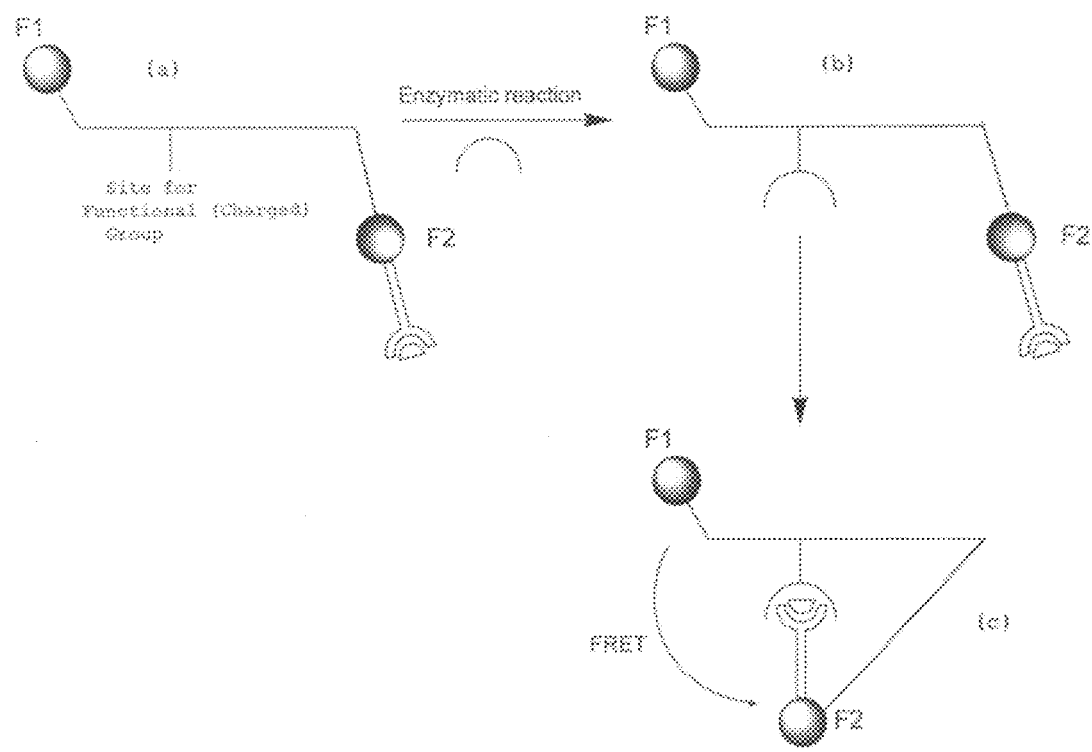
FIGS. 1A-1C are illustrations depicting intermolecular and intramolecular binding between a fluorescently labeled compound and a functional group added in an enzyme reaction to induce a Förster resonance energy transfer (FRET) interaction between an energy transfer pair.

The following terms and phrases shall have the definitions and meanings set forth below. Unless defined otherwise, all technical and scientific terms used herein have the same meaning as commonly understood to one of ordinary skill in the art.

As used herein, functional groups are chemical moieties which are added, lost or retained by a compound through chemical or biological modification. Functional groups include charged groups and uncharged groups. Nonlimiting examples of functional groups are phosphate, sulfonate, carboxyl, amine, sulfone, hydroxyl, acetyl, methyl, acyl, glycosyl, sulfate, thiol, amide and nitro.

As used herein, charged groups are functional groups which as chemical entities are charged and carry a valence which can be positive or negative at a given pH. Thus, charged groups include monoionic and polyionic groups or compounds, and more particularly, monocationic, polycationic, monoanionic and polyanionic groups or compounds. In accordance with the present invention, charged groups on biological molecules at physiological pH generally include phosphate, sulfonate, carboxyl, amine, sulfone, sulfate, thiol and amide groups. Nonlimiting examples of uncharged groups (at physiological pH) include methyl and acetyl groups.

As used herein, normalizing reagents are reagents or compounds that, when added to a mixture, serve to promote precipitation or co-precipitation of a compound. An example of a normalizing reagent is an unlabeled compound having a functional group. Such a normalizing reagent is particularly useful where there is only a small quantity of the labeled compound. There, the normalizing reagent provides a sufficient amount of the compound to promote precipitation. Depending on the compound to be precipitated, other examples of normalizing reagents include, without limitation, ions (e.g., metal ions) and solvents such as ethanol, methanol, isopropyl alcohol, dioxane, and combinations thereof.

As used herein, blocking agents or blockers are compounds, reagents or materials that block or mask functional groups, or sites where functional groups may be added, in compounds of interest, so that the functional group of interest can be identified. Blockers are useful where there is more than one site on a compound where a functional group can be added, such that adding functional groups to multiple sites can confound the assessment or quantification of a compound or an enzyme that adds the functional group. Blockers are also useful where there are multiple functional groups on a compound that cause the compound to precipitate, for example where a method requires that precipitation be used to separate a compound with one particular functional group from a compound without that functional group. Blocking agents can be utilized to block, for example, amine groups, sulfhydryl groups, aldehyde groups, carboxylate groups or phosphate groups. Blocking agents or blockers may be reversible or irreversible in nature.

As used herein, the singular forms "a", "an" and "the" are intended to include the plural forms as well, unless the context clearly indicates otherwise. Additionally, the use of "or" is intended to include "and/or", unless the context clearly indicates otherwise.

In some embodiments, a method for isolating a compound which has gained at least one functional group is provided. The method comprises (a) providing: (i) a compound which can gain a functional group, the compound comprising at least one non-radioactive signaling moiety; (ii) a chemical, enzymatic or catalytic source of the functional group which can be gained by the compound; and (iii) means to separate the compound which has gained the functional group from the compound which has not gained the functional group; (b) forming a mixture comprising the compound and the source of the functional group, and incubating the mixture under conditions suitable for the compound to gain the functional group; and (c) separating and thereby isolating any compound which has gained the functional group from any compound which has not gained the functional group. The separated compound can be further detected or quantified by detecting or quantifying the non-radioactive signaling moiety in the separated compound.

The present invention also encompasses the converse of the above method, i.e., a method for isolating a compound which has lost at least one functional group. This method comprises (a) providing: (i) a compound comprising a functional group and at least one non-radioactive signaling moiety; (ii) a chemical, enzymatic or catalytic source which can remove the functional group from the compound; and (iii) means for separating the compound which has lost the functional group from the compound which has not lost the functional group; (b) forming a mixture comprising the compound and the chemical, enzymatic or catalytic source and incubating the mixture under conditions suitable for the compound to lose the functional group; and (c) separating and thereby isolating any compound which has lost the functional group from any compound which has not lost the functional group.

These methods can be used with any compound known in the art that is capable of acquiring or losing a functional group. In various embodiments, the compound of interest comprises a macromolecule or a small biological compound, the latter being a compound naturally present in biological systems that is less than 2000, 1000 or 500 molecular weight. Nonlimiting examples of macromolecules and small biological compounds include nucleic acids, abasic nucleic acids, peptide nucleic acids, oligopeptides, polypeptides, proteins, sugars, oligosaccharides, polysaccharides, lipids, glycoproteins, glycolipids, proteoglycans, and lipoproteins. More specific examples of compounds contemplated herein for use in the present invention include lipids, glycolipids, lipoproteins, apolipoproteins, cytokines, hormones, sphingosines, sphingolipids, and ceram ides, for example glycosylceramides such as monosaccharide ceramides (e.g., glucosylceramide, and galactosylceramide), and disaccharide ceramides (e.g., lactosylceramide).

In some embodiments, the compound comprises a protein or an oligo- or polypeptide which is modified in post-translational modification. As used herein, an oligopeptide is a linear sequence of about 20 or less, about 19 or less, about 18 or less, about 17 or less, or about 16 or less amino acids. A multitude of post-translational modifications of peptides and proteins are known in the art. Nonlimiting examples of such post-translational modification reactions contemplated for use with the present invention include phosphorylation, acetylation, methylation, acylation, glycosylation, GPI anchor addition, hydroxylation, sulfation, disulfide bond formation, deamidation, and nitration.

In other embodiments, the compound comprises a non-biological compound, e.g., a synthetic or environmental compound. Nonlimiting examples include synthetic xenobiotics (e.g., TCDD), drugs, and petroleum products.

It is contemplated that these methods are particularly useful where the chemical, enzymatic or catalytic source of the functional group comprises an enzyme (e.g., a kinase) and a chemical comprising the functional group (e.g., ATP) that is utilized by the enzyme to add the functional group to the compound. As such, the present methods provide assays for a multitude of enzymes that add or remove functional groups from compounds including, for example, kinases, phosphatases, sulfatases, sulfotransferases, acetyltransferases, deacetylases, methylases, demethylases, carboxylases, decarboxylases, glycosylases, amidases, deamidases, aminases and deaminases.

In various embodiments, the methods are used to determine whether there is an enzyme in the sample that can add the functional group to the compound, e.g., a kinase or sulfotransferase. The methods are also useful for quantifying an enzyme activity in a sample. Also, the methods can be used to determine the presence or activity of inhibitors that inhibit enzymes that add or remove functional groups (see, e.g., Example 1). Alternatively, the methods can be used to determine the presence or quantity of a source of the functional group, e.g., ATP. In still another aspect, the methods are useful for detecting and identifying inhibitors to enzymes that add or remove functional groups.

In carrying out the present invention, it may be important to specifically differentiate between different isoforms of an enzyme, for example two kinase isoforms, e.g., sphingosine kinase 1 (SphK1) and sphingosine kinase 2 (SphK2). When using purified enzymes, this is usually not a problem. However, when carrying out assays with cell extracts or live cells, the simultaneous presence of more than one isoform can lead to measurements that are the sum of each individual isoform activity. Numerous solutions can be applied to obviate this problem in the course of running an assay under these conditions. For instance, there are differences in substrate specificity, for example, where SphK1 and SphK2 are differentiated by their ability of using enatomeric forms of sphingosine as a substrate where Sphk1 can use only the natural D-erythro form whereas SphK2 can use the L-threo form as well (Liu et al., Prog. Nucleic Acid Res. Mol. Biol. 71:493-511, 2002). Also, conditions can be adjusted that differentially affect each enzyme's activity, e.g., high salt inhibits SphK1 and stimulates SphK2, whereas Triton X-100 stimulates SphK1 and inhibits SphK2 (Liu et al 2002 op cit.). Lastly, inhibitors may be available that have specificity for one form of an enzyme versus the other. Thus, inhibitors that are selective for SphK2, such as SG14, have been described by Kim et al., Bioorganic Chemistry & Medicinal Chemistry 13:3475-3485 (2005) and an SphK1 specific inhibitor has been described in US Patent Publication No. 2010/0035959 A1 and Paugh et al., Blood 15:1382-1391 (2008). An assay may thus be carried out where no inhibitor is added to give the total amount of enzyme activity and each of the isoform specific inhibitors can be added to give the amount of activity contributed by the unblocked isoform. Elimination of one activity or another to separately test a selected isoforms may also be carried out by the use of null mutants (Allende et al., JBC 279:52487-52492, 2004; Kharel et al., JBC 280:36865-36872, 2005; Zemann et al., Blood 107:1454-1458, 2006; Michaud et al., FEBS Letters 580:4607-4612, 2006) or by transfection with siRNA directed toward one isoform (Klawitter et al., Br J Pharmacol 150:271-280, 2007; Lai et al., J Immun 183:2097-2103, 2009).

It is also contemplated by the present invention that isoforms may be distinguished by using different substrates. For example, assays with sphingosine kinase may also be carried out with sphinganine and/or phytosphingosine substrates since both are recognized by SphK2 (Liu 2002 op. cit.).

These methods can be utilized with any sample. The sample utilized for these methods can be derived or taken from any source, including any biological or non-biological source, such as clinical samples, for example, blood urine, feces, saliva, pus, semen, serum, other tissue samples, fermentation broths, culture media, and environmental sources, for example, plant material, soil and the like. If necessary, the analyte may be pre-extracted or purified by known methods to concentrate or isolate biological components, or eliminate interfering substances. Non-biological sources include, for example, environmental sources and industrial sources such as ground water, oil spill sites, industrial effluent, waste treatment sites, etc.

The separation of the compound with the functional group from the compound without the functional group can utilize any method. Examples include precipitation, capture, phase separation, chromatography, electrophoresis, and the like, all of which are known in the art.

In some embodiments, the separating means comprises differential precipitation. A precipitation reaction is a chemical reaction in which a solid forms from solution. The solid is called the precipitate. A precipitate forms if any possible combination of ions in a solution forms a salt that is insoluble in water. That is, a precipitate is a salt that is no longer solvated by water.

It is understood that, for optimum precipitation of the compound having the charged functional group while minimizing precipitation of the compound without the charged functional group, the proper solution conditions (e.g., buffer salt, pH and molarity) must be utilized. Such conditions are known in the art or can be determined without undue experimentation for any particular compound.

A number of ions are known in the art as being capable of precipitating or co-precipitating a compound comprising a charged functional group, including, for example, any of the metals from Group IIIB, Group IVB or the Lanthanide Series, and combinations thereof. The metals of Group IIIB include scandium (Sc), yttrium (Y), lanthanum (La) and actinium (Ac). The metals of Group IVB include titanium (Ti), zirconium (Zr), hafnium (Hf) and rutherfordium (Rf). Among the metals of the Lanthanide Series are cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Th), ytterbium (Yb) and lutetium (Lu). In some embodiments, for example where the compound comprises a phosphate functional group, lanthanide and zirconium are particularly useful. Barium is also useful for precipitation of phosphate containing compounds. See, e.g., Example 1.

In some embodiments, optionally after washing, the label is detected in the precipitate. In other embodiments, optionally after washing, the precipitate is solubilized and the label is detected in solution. Resolubilization schemes for many precipitates are known in the art. For example, a barium precipitate of a phosphate-containing compound may be solubilized with EDTA, since EDTA has a higher affinity for barium than phosphate. See, e.g., Example 1.

As an alternative to precipitation, a compound having a functional group can be separated from the compound without the functional group by differentially capturing the compound with the functional group on a matrix that binds the functional group. Techniques and formats for capturing analytes and probe-containing materials are known. See, e.g., U.S. Pat. Nos. 6,221,581 and 7,064,197; U.S. Patent Publication No. 20100160182; Loomans et al., Assay and Drug Develop Tech 1:445-453 (2003); Barnouin et al., Proteomics 5: 4376-4388 (2005); and Lee et al., Prostaglandins & other Lipid Mediators 84:154-162 (2007). In these embodiments, once captured, the un-bound compounds can be washed away and signal from the captured moiety can be directly observed by fluorescence detection.

Retention on a matrix may involve nonspecific background material in which unmodified substrate may bind to the matrix and elicit a false signal. In using fluorescent labels or markers on a matrix, such fluorescent components should be minimized so that they do not quench the fluorescent signal.

As an illustration of capture techniques, methods and techniques are known for capturing free-amine functionalities in proteins or peptides that are based on plates (support surfaces), resins or gels. Among the various methods and techniques known in the art for capturing amine groups in macromolecules are maleic anhydride-activated plates, aldehyde-activated agarose beads, CDI-activated agarose, AccQ-Tag Ultra columns, and CM-Sephadex and CM-Sepharose columns. Matricies that bind various other functional groups are also known. For example, compounds with phosphate functional groups can be isolated on a matrix comprising a metal ion, for example $Fe^{+3}$, $Ga^{+2}$, $Zn^{+3}$, $Zn^{+2}$, or $Mn^{+2}$. See, e.g., Kinoshita et al., Mol. Cell. Proteomics 5:749-757 (2006).

As briefly discussed above, a blocker is often useful for blocking at least one moiety on the compound that interferes with the compound gaining the functional group, e.g., where there are multiple sites where the functional group can attach, and/or a moiety that interferes with the separation step, e.g., where there are moieties that allow precipitation or capture of a compound without the functional group to which the precipitation or capture is to be directed.

Blockers are known that can block many specific functional groups in compounds and macromolecules including, for example, amine groups, sulfhydryl groups, aldehyde groups, carboxylate groups and phosphate groups. Blocking agents or blockers may be reversible or irreversible in nature, meaning that their effects can be reversed in some instances to unblock or unmask the groups or sites of blocking, or their effects are not reversible in other instances so that the blocked or masked groups or sites cannot be unblocked or unmasked easily or practically.

Nonlimiting examples of blocking agents or blockers for specific functional groups include the following:
1. Blocking Amine Groups ($NH_2$)
Irreversible: Sulfo-NHS acetate; Acetic anhydride
Reversible: Citraconic anhydride; Maleic anhydride
2. Blocking Sulfhydril Groups (SH)
Irreversible: N-ethylmaleimide; Iodoacetamide
Reversible: Sodium tetrathionate; Ellman's reagent [5,5'-dithio-bis-(2-nitrobenzoic acid) or DTNB]; Dipyridyl disulfide
3. Blocking Aldehyde Groups
Irrevesible: Reductive amination with Tris or ethanolamine
Revesible: Imine formation
4. Blocking Carboxylate Groups
Esters or amides using carbodiimide activation
5. Blocking Phosphate Groups
Reversible: Use of 2-cyanoethyl
Commonly used blocking groups for hydroxyl functionality include the following:
6. Blocking Ethers
Methyl ether. In practice, this group is generally irreversible since it requires harsh conditions for deprotection.
Tetrahydrofuranyl ether. This group can be cleaved under mild acidic conditions.
Trimethylsilyl ether. This group can be cleaved by fluoride ion easily.
t-Butyldimethylsilyl ether. This group can be cleaved by fluoride ion easily.
7. Blocking Esters
formate, acetate, chloroacetate, trichloroacetate, Trifluoroacetate.
8. Blocking Carbonates
alkyl methyl carbonate, methoxy methyl carbonate, alkyl allyl carbonate, alkyl p-nitrophenyl carbonate.
9. Blocking Sulfonates
allyl sulfonate, benzylsulfonate, tosylate, methanesulfonate.

Non-radioactive detection can be carried out using labels, signaling moieties and methods known in the art and appropriate for the signaling moiety utilized in the assay. These include direct and indirect signaling methods. Direct signaling methods and labels can utilize, for example, fluorescent compounds, phosphorescent compounds, chemiluminescent compounds, chromogenic compounds, chelating compounds, electron dense compounds, magnetic compounds, energy transfer compounds or intercalating compounds, or a combination of any of the foregoing. Indirect signal methods and labels can utilize, for example, antibodies, antigens, haptens, receptors, hormones, ligands or enzymes, or a combination of any of the foregoing.

As is known in the art, the methods can use binding partners in connection with non-radioactive detection. To this end, such binding partners can include, for example, pairs comprising sugars/lectins, antigens/antibodies, ligand/receptor, hormone/receptor, enzyme/substrate, biotin/avidin, biotin/streptavidin, haptens/antibodies (e.g., digoxygenin/anti-digoxygenin), or combinations of any of the foregoing.

Examples of fluorescent dyes useful for the instant methods include xanthene dyes, rhodamine dyes, fluorescein dyes, cyanine dyes, asymmetric cyanine dyes, phthalocyanine dyes, squarene dyes, acridone dyes, quinacridone dyes, bodipy dyes, nitrobenzoxadiazole dyes and fluorescent proteins. When more than one fluorescent label is used, e.g., if performing the methods to detect enzymes for more than one functional group, or if combining the method with another assay that utilizes fluorescent dyes, it is important to choose fluorescent moieties with different extinction coefficients and spectra characteristics.

These methods can be carried out in solution as a one step homogeneous assay or as a two step assay involving a matrix or solid support in which one or more washing steps are used.

In various embodiments of the present invention, the methods are carried out in a homogenous format. In other assays, the means to separate the functionalized compound from the non-functionalized compound utilizes a matrix that binds the functional group, for example a matrix comprising a dinuclear metal (e.g., $Zn^{+2}$ or $Mn^{+2}$) to bind a phosphate functional group (Kinoshita et al., Mol. Cell. Proteomics 5:749-757, 2006). Detecting the label on the labeled compound bound to the matrix can be carried out either directly or indirectly.

In performing the assay either on a solid matrix or in solution, tubes or microtiter plates can be used to hold the mixture containing the various components.

Kits may be designed and assembled for the purpose of carrying out the present invention where a non-radioactively labeled kinase substrate is provided. Reagents for performing the precipitation step may also be provided in such kits or one or more of these they may be left to the user to provide.

One embodiment of these methods is described in Example 1, describing an assay for sphingosine kinase comprising combining fluoresceinated sphingosine, ATP and the kinase to form fluoresceinated sphingosine-1-phosphate, which was then quantitatively precipitated with barium acetate and ethanol. In some cases, a normalizing reagent in the form of unlabeled sphingosine-1-phosphate was added. After washing, the precipitated reaction product was resolubilized and fluorescence was measured. Quantitative precipitation of the phosphorylated reaction product was noted, both with and without the normalizing reagent.

Another embodiment of these methods is described in Example 2, describing an assay for the kinase AKT1 comprising combining the fluoresceinated 11-mer oligopeptide crosstide, ATP and AKT1 to form fluoresceinated crosstide phosphate, which was then quantitatively precipitated with lanthanum. A normalizing reagent (unfluoresceinated crosstide phosphate) was used. After washing, the precipitated reaction product was resolubilized and fluorescence was measured. Quantitative precipitation of the phosphorylated reaction product was noted.

Still another embodiment of these methods is described in Example 3, where precipitation of a fluoresceinated, sulfated peptide is demonstrated, showing that a compound with a monovalent anion (sulfate) can be selectively precipitated away from the unmodified peptide.

The three examples provided establish that the instant methods can be utilized to detect and quantify any small molecule or macromolecule having a charged functional group.

In some embodiments, non-radioactive signaling moieties are utilized that form energy transfer pairs, where the signal is influenced by Förster resonance energy transfer (also known as fluorescence resonance energy transfer, or FRET). FRET uses two fluorophores (an energy transfer pair) where the emission spectrum of one fluorophore (the donor) is of higher energy (having a shorter wavelength) and overlaps the absorption spectrum of the other fluorophore (the acceptor). When the two fluorophores are brought within about 10-100 Å and the donor fluorophore is excited, the energy of the donor is transferred to the acceptor by a resonance induced dipole-dipole interaction. This interaction is observed by fluorescence quenching of the donor fluorophore and/or emission of the acceptor fluorophore. See, e.g., discussion in U.S. Pat. No. 6,117,635 and references cited therein.

The FRET interaction forms the basis of additional methods of this invention. In these methods, a non-radioactive signaling moiety comprises the two members of an energy transfer pair. At least one of the two members of the energy transfer pair is on a compound, within 10-100 Å of a site where a functional group (e.g., a phosphate) can be attached, e.g., by a kinase. The second member of the energy transfer pair has a charge opposite to the functional group (if the functional group is charged, e.g., a phosphate or sulfate) or to the moiety that a neutral functional group is bound (e.g., where a methyl or acetyl group is bound to an amino moiety). A FRET interaction thus occurs where the second member of the energy transfer pair binds by charge interaction to the charged functional group or moiety. This can be observed by a quenching of the fluorescence of the donor or an excitation of the acceptor. This forms the basis for methods of determining (1) the addition of a charged functional group to an uncharged moiety on a compound, (2) the removal of a charged functional group from an uncharged moiety on a compound, (3) the addition of an uncharged functional group to a charged moiety on a compound, and (4) the removal of an uncharged functional group from a charged moiety on a compound. Details of these methods are as follows.

In some embodiments, the present invention provides a method for determining the addition of a charged functional group to an uncharged moiety on a compound. The method comprises (a) providing: (i) the compound without the functional group, wherein the compound further comprises one member of an energy transfer pair; (ii) a second member of the energy transfer pair, having a charge opposite to the charge of the functional group; and (iii) a chemical, enzymatic or catalytic source of the functional group capable of adding the functional group to the compound; (b) forming a mixture comprising the compound without the functional group, the second member of the energy transfer pair, and the source of the functional group and incubating the mixture under conditions suitable for the compound to add the functional group; and (c) detecting a FRET interaction between the members of the energy transfer pair, wherein the presence of the FRET interaction is indicative of the addition of the functional group to the compound.

In other embodiments, a method of determining the addition of an uncharged functional group to a charged moiety on a compound is provided. The method comprises (a) providing (i) the compound without the functional group, wherein the compound further comprises one member of an energy transfer pair; (ii) a second member of the energy transfer pair, having a charge opposite to the charge of the moiety; and (iii) a chemical, enzymatic or catalytic source of the functional group capable of adding the functional group to the charged moiety; (b) forming a mixture of the compound without the functional group and the source of the functional group and incubating the mixture under conditions suitable for the compound to add the functional group to the charged moiety; (c) adding the second member of the energy transfer pair to the mixture of step (b); and (d) evaluating the energy transfer pair to determine the degree to which a FRET interaction occurs, wherein the addition of the functional group to the charged moiety causes a reduction in the FRET interaction.

Further provided is a method for determining the removal of a charged functional group from an uncharged moiety on a compound of interest. The method comprises (a) providing: (i) the compound of interest with the functional group, wherein the compound further comprises one member of an energy transfer pair; (ii) a second member of the energy transfer pair, having a charge opposite to the charge of the functional group; and (iii) a means to remove the functional group from the uncharged moiety; (b) forming a mixture of the compound of interest with the functional group and the means to remove the functional group and incubating the mixture under conditions suitable for the functional group to be removed from the compound; (c) adding the second member of the energy transfer pair to the mixture of step (b); and (d) determining whether a FRET interaction is occurring between the members of the energy transfer pair, wherein the absence of a FRET interaction indicates that the charged functional group has been removed from the uncharged moiety by the means to remove the functional group.

Additionally, a method for determining the removal of an uncharged functional group from a charged moiety on a compound is provided. The method comprises (a) providing: (i) the compound with the functional group, wherein the compound further comprises one member of an energy transfer pair; (ii) a second member of the energy transfer pair, having a charge opposite to the charged moiety; and (iii) a means to remove the functional group from the charged moiety; (b) forming a mixture comprising the compound with the functional group, the second member of the energy transfer pair, and the means to remove the functional group from the charged moiety and incubating the mixture under conditions suitable for the functional group to be removed from the compound; (c) determining whether a FRET interaction is occurring between the members of the energy transfer pair, wherein the presence of a FRET interaction indicates that the uncharged functional group has been removed from the charged moiety by the means to remove the functional group.

Figure 1B:
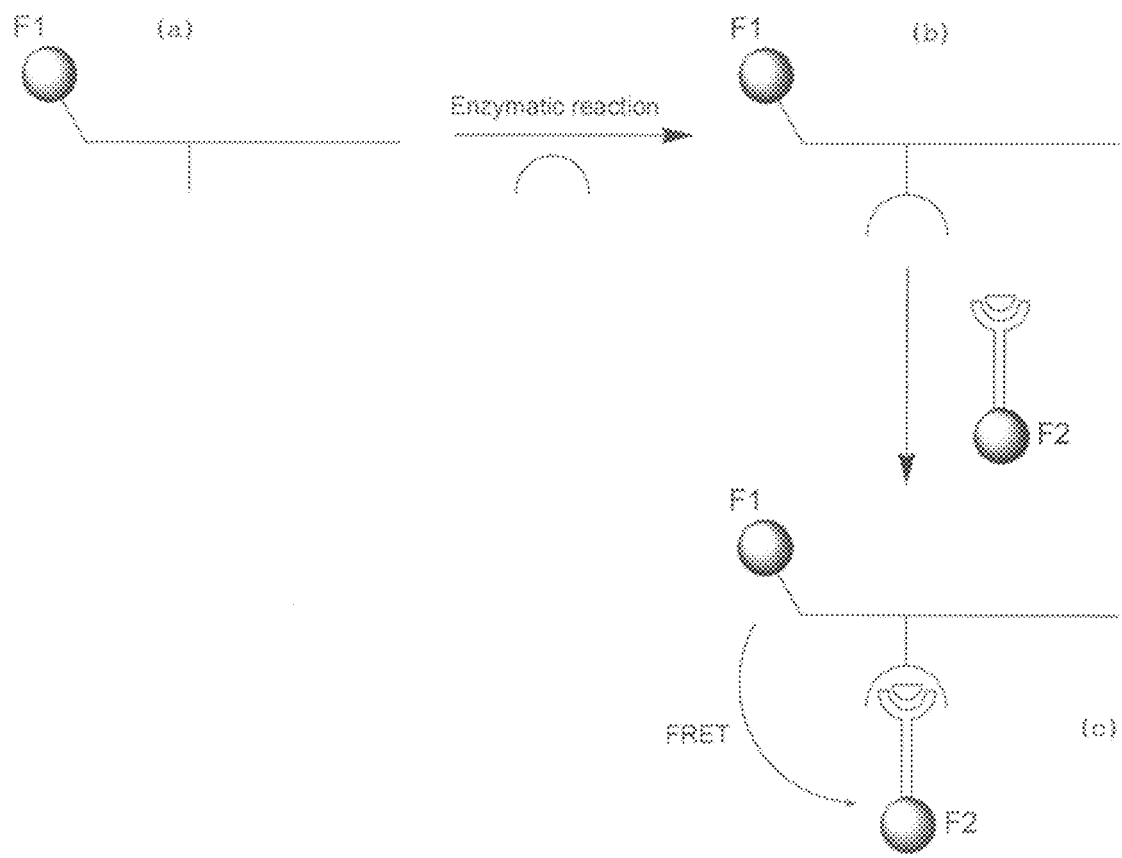
Figure 1C:
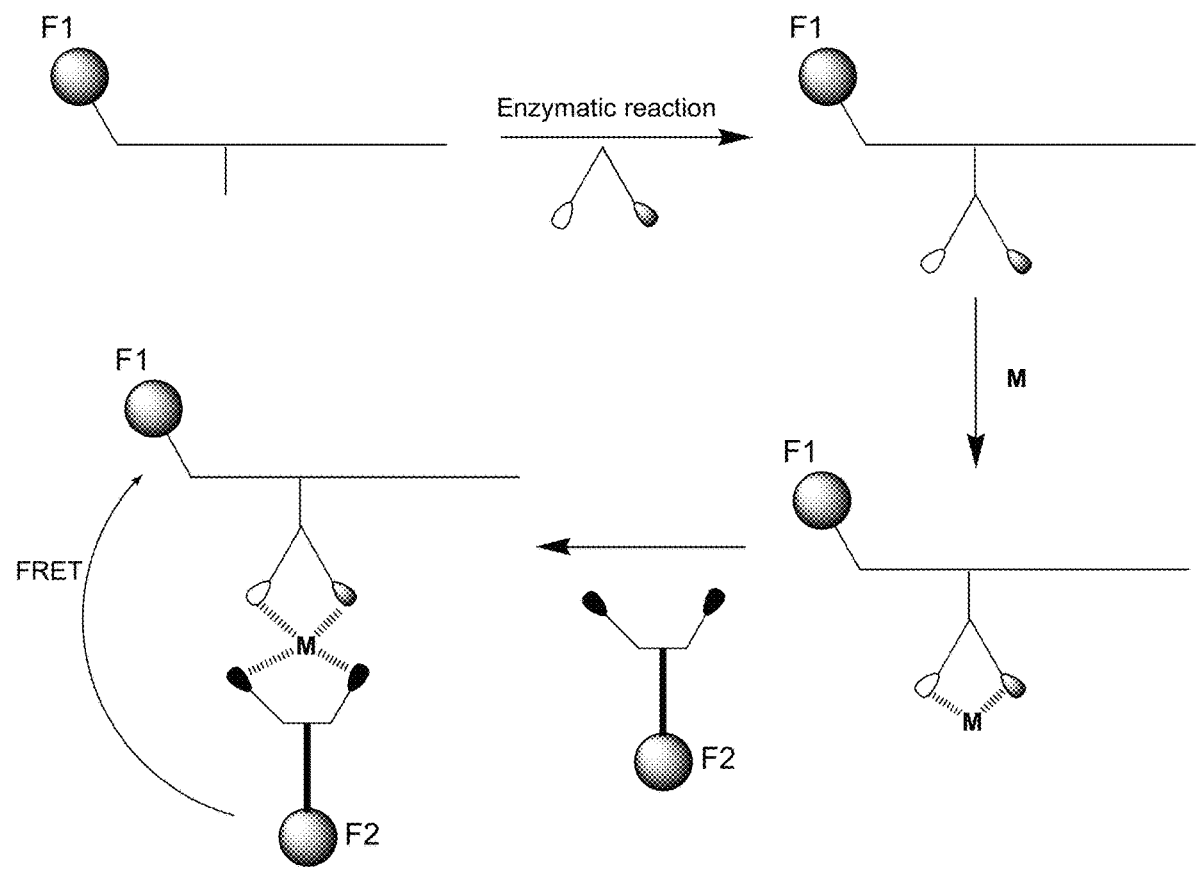

The detection of a compound with a charged functional group by these methods is illustrated in FIGS. 1A-1C. In these embodiments, the assay can use an intramolecular interaction (FIG. 1A) or an intermolecular interaction (FIG. 1B). It is noted that an intermolecular interaction can occur in the configuration illustrated in FIG. 1A, since the F2 group on one molecule can bind to the functional group on another molecule. When the functional group is not added to the molecule of interest, as depicted in (a), energy transfer pair members F1 and F2 are too far apart to undergo a FRET interaction. Upon addition of the charged functional group (denoted as a half circle), as depicted in (b), a moiety of the opposite charge that is on F2 (denoted as an open stem and cup-like structure) binds noncovalently to the functional group by charge interaction, as depicted in (c), bringing F1 and F2 close enough to cause a FRET interaction. As discussed above, this FRET interaction can be detected upon excitation of the energy donor (which can be either F1 or F2) by quenching of emittance (e.g., fluorescence) from the energy donor due to energy transfer to the acceptor, or by emittance (e.g., fluorescence) of the acceptor.

In these embodiments, the charge on the moiety on F2 is of opposite polarity as the charge of the added functional group, in order for the moiety to bind to the functional group, bringing F1 and F2 close enough to allow a FRET interaction. Thus, where a negatively charged functional group is added, for example a phosphate, carboxyl, sulfate, nitro, or acyl group, a positively charged dye (F2) is utilized. Conversely, where a positively charged functional group is added, e.g., where an amino group is added in an amination reaction, a negatively charged dye (F2) is used. A majority of fluorescent energy transfer dyes are negatively charged, with other fluorescent energy transfer dyes, such as sulfonamide dyes, being positively charged. Among such positively charged sulfonamide dyes are those disclosed in U.S. Pat. Nos. 7,569,695 and 7,737,281. Still other dyes are uncharged.

In some embodiments, the added functional group is uncharged, for example in a methylation or an acetylation reaction. Where the uncharged group is added to a charged moiety (e.g., an amino group), those functionalization reactions can be detected using the same formats as illustrated in FIGS. 1A-1C, except the functionalization reaction results in a lack of a FRET interaction, and the control reaction, where the charged moiety is unmodified, would be detected as a FRET interaction. Thus, the methylation or acetylation reaction is detected by an increase in the energy donor emittance (e.g., fluorescence) (due to cessation of quenching) or a decrease in the energy acceptor emittance (e.g., fluorescence) (due to a cessation of energy transfer from the donor).

In other embodiments, a FRET interaction is utilized to detect the removal of a functional group from a compound of interest. The methods and compositions depicted in FIGS. 1A-1C are also used here. Where a charged group is removed to leave an uncharged moiety on the compound of interest, for example with the action of a phosphatase, a sulfatase, a deaminase, a decarboxylase, a deamidase or a deaminase, the assay works in the reverse direction from that depicted in FIGS. 1A-1C. Before the removal of the functional group, the reagents of FIGS. 1A-1C have the configuration of (c), due to the interaction of the charged group with F2. This is detected by a FRET interaction, where the energy donor emittance (e.g., fluorescence) is quenched. With removal of the functional group, the FIGS. 1A-1C reagents are as in (a) since the neutral moiety where the functional group was removed does not interact with the charged F2 dye. Thus, the action of an enzyme that removes a charged functional group to leave a neutral moiety on the compound of interest is detected by the elimination of a FRET interaction.

Conversely, the removal of an uncharged group to leave a charged moiety on the compound of interest, for example the removal of a methyl or acetyl group from an amino moiety (e.g., an ε amino group of a lysine residue on a protein) by a demethylase or deacetylase, can be detected by utilizing the reagent depicted in (a) of FIG. 1A or 1B. The compound of interest with the uncharged functional group, prepared as a FIGS. 1A-1C reagent, has the configuration of (a), since the charged F2 dye does not interact with the uncharged functional group. As discussed above, there is no FRET interaction in the step (a) configuration. Upon removal of the uncharged functional group, leaving a charged moiety, the reagent takes on the configuration of (c), where a FRET interaction takes place, due to the interaction of the charged moiety with the oppositely charged F2 dye. Thus, the removal of the functional group is detected by the presence of the FRET interaction, e.g., the quenching of the energy donor of the FRET pair.

For any of the above-described methods, where the F2 dye is not covalently joined to the compound, as depicted in FIG. 1B, the F2 dye can be added before the mixture is incubated or after the mixture is incubated. The latter option is useful if the preferred incubation conditions (e.g., temperature, pH, molarity, buffering capacity) to promote enzyme action to add or remove the functional group are different from the preferred conditions under which the F2 dye binds and the FRET interaction occurs. An important consideration here is that the pH under which the F2 dye binds must be such that the F2 dye and the functional group or moiety are charged or uncharged as needed. Such incubation conditions can be determined for any particular enzyme, compound, and electron transfer pair without undue experimentation.

When designing the particular configurations for these methods, care should be taken to minimize interference to the method's proper execution. Such interference can come from several sources. In the first instance, interference could come from the source of the functional group (e.g., ATP for a kinase reaction). Since in most cases that source has the same charge as the functional group on the compound (for example, ATP is negatively charged, as is a phosphate functional group transferred from ATP to the compound by a kinase), that source competes with the functional group transferred to the compound for binding to the F2 dye. Such interference can be addressed by means known in the art, for example by minimizing the concentration of the source, and/or by utilizing the intermolecular configuration as depicted in FIG. 1B, and/or by adjusting the conditions after incubation to minimize the effect of the source interference, e.g., by adjusting the pH or molarity of the solution, and/or by separating the compound from the source (for example by ultrafiltration or precipitation).

Depending on the structure of the compound, another source of interference can be from charged groups on the compound, which could bind nonspecifically to the F2 dye. This interference can be avoided by use of a blocker to block the charged groups on the compound, and/or by utilizing an intramolecular configuration as depicted in FIG. 1A, such that the F2 moiety is sterically prevented, for example with a linker moiety, from interacting with charged moieties other than the desired functional group.

An additional source of interference can come from nonspecific interactions (i.e., stickiness) between the F1 fluorophore and the F2 fluorophore, where F1 and F2 are either on the same compound or on different compounds. Such nonspecific interactions can be resolved by the use of an F1 dye that has the same charge as the F2 dye, or by using an F1 dye with a neutral charge. When the F1 dye has the same charge as the F2 dye, care should be taken to minimize interaction of the F1 dye with the functional group on the same compound or on a different compound.

In some embodiments, the fluorescent dye that interacts with the functional group (F2 in FIGS. 1A-1C) further comprises a moiety that covalently or noncovalently binds to the functional group. An example is a metal chelator which, in the presence of a metal ion that binds to the functional group, will promote the binding of the functional group to the fluorescent dye. This is illustrated in FIG. 1C, where the enzymatic reaction adds a functional group (e.g., phosphate) that can bind metal ion (M) to the compound. With the addition of the metal ion and F2 comprising a chelator (illustrated as two arms with black knobs), the metal ion binds to the chelator and the functional group, bringing the F2 dye to the proximity of the F1 dye, allowing a FRET interaction. A nonlimiting example of such chelators is the lanthanum (a phosphate binding metal) chelators described in U.S. Pat. No. 5,656,433. Although FIG. 1C shows the metal ion binding to the functional group before binding to the chelator-F2 complex, the opposite could occur— the chelator-F2 complex could be first mixed with the metal ion, allowing the metal ion to bind to the complex first, and this could then be added to the enzyme reaction mix.

As with the previously described methods, these methods can be used with any compound known in the art that is capable of acquiring or losing a functional group. In various embodiments, the compound of interest comprises a macromolecule or a small biological compound, the latter being a compound naturally present in biological systems that are less than 2,000, 1,000 or 500 molecular weight. Nonlimiting examples of macromolecules and small biological compounds include nucleic acids, abasic nucleic acids, peptide nucleic acids, oligopeptides, polypeptides, proteins, sugars, oligosaccharides, polysaccharides, lipids, glycoproteins, glycolipids, proteoglycans, and lipoproteins.

In some embodiments, the compound comprises a protein or an oligo- or polypeptide which is modified in post-translational modification. In other embodiments, the compound comprises a non-biological compound, e.g., a synthetic or environmental compound.

It is contemplated that these methods are particularly useful where the source of the functional group comprises an enzyme (e.g., a kinase) and a chemical comprising the functional group (e.g., ATP). As such, these methods provide assays for a multitude of enzymes that add or remove functional groups from compounds including, for example, kinases, phosphatases, sulfatases, sulfotransferases, acetyltransferases, deacetylases, methylases, demethylases, carboxylases, decarboxylases, glycosylases, amidases, deamidases, aminases and deaminases.

In various embodiments, the methods are used to determine whether there is an enzyme in the sample that can add the functional group to the compound, e.g., a kinase, phosphatase, or sulfotransferase. The methods are also useful for quantifying an active enzyme in a sample. Also, the methods can be used to determine the presence or activity of inhibitors that inhibit enzymes that add or remove functional groups (see, e.g., Example 1). Alternatively, the methods can be used to determine the presence or quantity of a source of the functional group, e.g., ATP. In still another aspect, the methods are useful for detecting and identify inhibitors to enzymes that add or remove functional groups.

Also provided are reagents for determining the presence of an enzyme that adds or removes a charged functional group to an uncharged moiety on a substrate. The reagents comprise the substrate to which a first member and a second member of an energy transfer pair are covalently bound at a distance such that a FRET interaction does not occur unless the charged functional group is present, wherein the second member of the energy transfer pair has a charge opposite to the charge of the functional group, and wherein the presence of the charged functional group to the substrate causes noncovalent binding of the second member of the energy transfer pair to the functional group, bringing the first member and the second member of the energy transfer pair close enough so that a FRET interaction occurs.

These reagents are particularly useful for the relevant methods described above that utilize a FRET interaction. As such, the scope of these reagents is contemplated to be the full scope that is useful for any of the above-described methods that utilize FRET and a charged functional group. Thus, the substrate can be any substrate for any enzyme that adds or removes a charged functional group to an uncharged moiety. In some embodiments, the substrate is a macromolecule or a small biological compound, for example a protein or an oligo- or polypeptide which is modified in post-translational modification. In other embodiments, the compound comprises a non-biological compound, e.g., a synthetic or environmental compound. Nonlimiting examples of enzymes that catalyze the addition or removal of the charged functional group to the substrate include kinases, phosphatases, sulfatases, sulfotransferases, carboxylases, decarboxylases, glycosylases, amidases, deamidases, aminases and deaminases.

In various embodiments, the second member of the energy transfer pair further comprises a chelator that chelates a metal that binds to the functional group, as discussed above.

Additionally, a reagent for determining the presence of an enzyme that adds or removes an uncharged functional group to a charged moiety on a substrate is provided. The reagent comprises the substrate to which a first member and a second member of an energy transfer pair are covalently bound at a distance such that a FRET interaction does not occur unless the uncharged functional group is absent, wherein the second member of the energy transfer pair has a charge opposite to the charge of the moiety, and wherein the absence of the uncharged functional group causes noncovalent binding of the second member of the energy transfer pair to the charged moiety, bringing the first member and the second member of the energy transfer pair close enough so that a FRET interaction occurs.

These reagents are also useful for the relevant methods described above that utilize a FRET interaction. As such, the scope of these reagents is contemplated to be the full scope that is useful for any of the above-described methods that utilize FRET and an uncharged functional group. Thus, the substrate can be any substrate for any enzyme that adds or removes an uncharged functional group to a charged moiety. In some embodiments, the substrate is a macromolecule or a small biological compound, for example a protein or an oligo- or polypeptide which is modified in post-translational modification. In other embodiments, the compound comprises a non-biological compound, e.g., a synthetic or environmental compound. Nonlimiting examples of enzymes that catalyze the addition or removal of the uncharged functional group to the substrate include acetyltransferases, deacetylases, methylases and demethylases.

Preferred embodiments are described in the following examples. Other embodiments within the scope of the claims herein will be apparent to those skilled in the art from consideration of the specification or practice of the invention as disclosed herein. It is intended that the specification, together with the examples, be considered exemplary only, with the scope and spirit of the invention being indicated by the claims, which follow the examples.

Example 1

Detection of Sphingosine-1-Phosphate

Introduction

An assay is described herein where the compound sphingosine-1-phosphate, labeled with a fluorescent dye, is separated from dye-labeled sphingosine by precipitating the phosphorylated compound under conditions where the unphosphorylated compound is not precipitated. The precipitate is separated from the unprecipitated sphingosine, then solubilized, and the dye is quantified, thus quantifying the phosphorylated compound. This assay is particularly useful for detecting and quantifying sphingosine kinase activity.

Sphingosine is 18-carbon amino alcohol with an unsaturated hydrocarbon chain having the structure

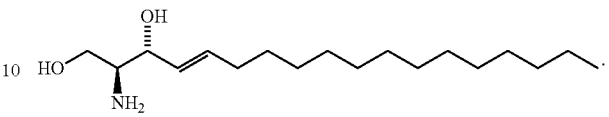

Sphingosine is phosphorylated at the non-polar end by the enzymes sphingosine kinase 1 and sphingosine kinase 2, to form sphingosine-1-phosphate (S1P). S1P is an important signaling molecule, and serves in particular as a major regulator of vascular and immune systems. See, e.g., Lloyd-Evans et al., Nat. Med. 14:1247-1255 (2008); Ryu et al., EMBO J. 25:5840-5851 (2006); Maceyka et al., J. Lipid Res. 50:S272-S276 (2009); Peterson et al., Proc. Natl. Acad. Sci. USA 105:20764-20769; and U.S. Pat. No. 6,730,480. Thus, the detection of S1P and the sphingosine kinases is important for the understanding of the various systems that S1P influences. Current methods for separating sphingosine from S1P generally use chromatographic, electrophoretic or spectrometric methods. See, e.g., Bandhuvula et al., Biochem. Biophys. Res. Commun. 380:366-370 (2009); Lee et al., Anal. Chem. 80:1620-1627 (2008); Jin et al., Arch. Pharm. Res. 29:1049-1054 (2006); Jin et al., Anal. Biochem. 380:35-40 (2008); Berdyshev et al., Anal. Biochem. 339:129-136 (2005); Caligan et al., 2000, Anal. Biochem. 281:36-44 (2000); and Yatomi, Biochim. Biophys. Acta 1780:606-611 (2008).

Materials and Methods

The following sphingosine kinase reaction mix (50 µl) was prepared:
  50 mM Tris HCl pH 8.0
  150 mM NaCl
  10 mM $MgCl_2$
  1.0 mM DTT
  7.5 µM Sphingosine fluoresceine
  500 µM ATP
  0.16 units human sphingosine kinase 1 (hSK1).
The same mix was also prepared without the enzyme, as a control and for titration studies, as further described below.

The reaction mix was incubated 1 h at 37° C.

The S1P formed by the enzyme was then precipitated in the reaction mix by the addition of 5 µl of 1 M barium acetate+300 µL of 100% ethanol, followed by 30 min incubation on ice. In some cases, 5 µl of 1 mg/ml S1P (without dye) was added as a carrier (normalizing reagent) to facilitate precipitation of the sphingosine phosphate formed. After the precipitation step, the reaction mix was vortexed and transferred to a nylon 0.22 µm filter tube and centrifuged at 4000×g for 2 minutes. The filter tube was then washed twice with 200 µl 70% ethanol in 1.5% Triton® X-100. The precipitate was then solubilized and eluted from the filter with 2×100 µl of 20 µM EDTA+100 mM Tris HCl ph 8.0+5% Triton® X-100. The eluted fluoresceinated S1P was quantified by measuring intensity of fluorescence. Preliminary studies established that the two wash steps were sufficient to remove essentially the entire quantity of unprecipitated sphingosine fluorescein.

Results and Discussion

Figure 2:
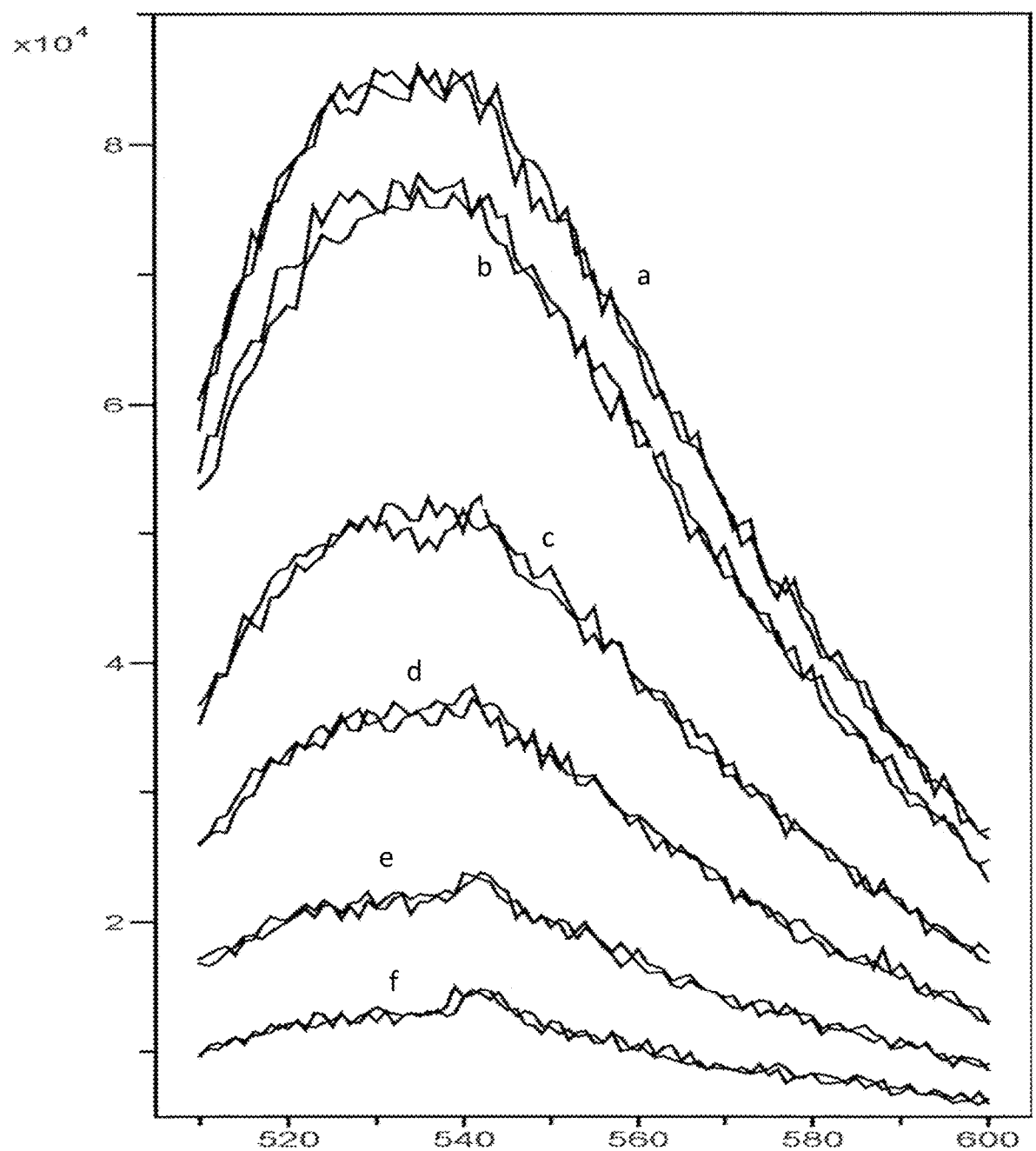
FIG. 2 is a graph showing the results of a sphingosine kinase 1 assay using six different dilutions of the enzyme, where no carrier was used when precipitating the product of the reaction.

The fluorescein-S1P assay described above was first performed without and with the S1P carrier to determine the effect of the carrier on the completeness of the precipitation step. Mixtures of the reaction mix with and without hSK1 were prepared, incubated, precipitated, washed, and eluted, then fluorescence emission was scanned from 510-600 nm. FIG. 2 shows results where carrier was not added. The lines labeled "a" show the results of two replications where 50 µl reaction mix with enzyme was used without adding any reaction mix without enzyme; in "b", 40 µl reaction mix with enzyme and 10 µl reaction mix without enzyme mix was used; in "c", 30 µl reaction mix with enzyme and 20 µl reaction mix without enzyme was used; in "d" 20 µl reaction mix with enzyme and 30 µl reaction mix without enzyme was used; in "e" 10 µl reaction mix with enzyme and 40 µl reaction mix without enzyme was used; in "f" 5 µl reaction mix with enzyme and 45 µl reaction mix without enzyme was used. As shown in FIG. 2, where 50 µl reaction mix with enzyme was used without any reaction mix without enzyme ("a"), the peak of the fluorescence had an intensity of about 85,000 fluorescence counts/sec.

Figure 3:
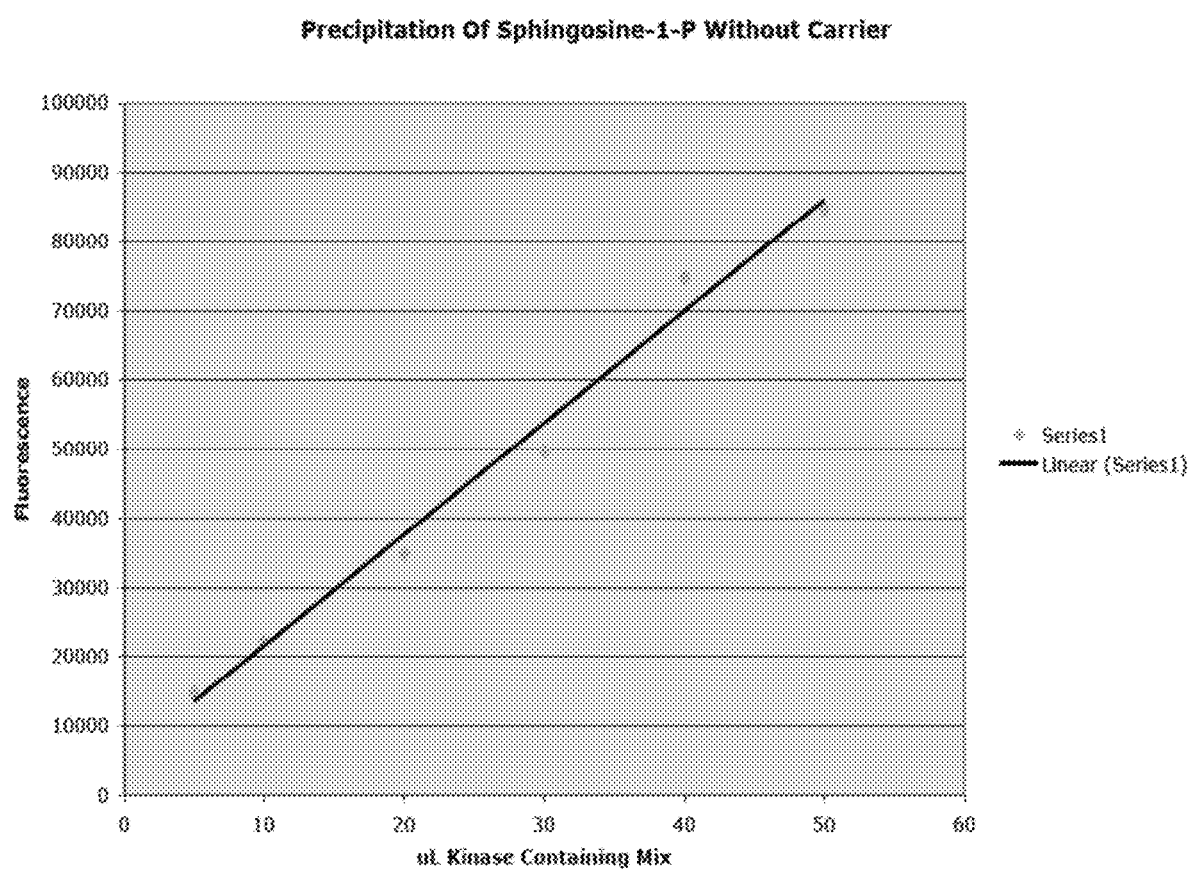
FIG. 3 is a graph of the peak results from each assay where the results are shown in FIG. 2.

A graph of the peak results from these assays is shown in FIG. 3. The assay without carrier shows linear results.

Figure 4:
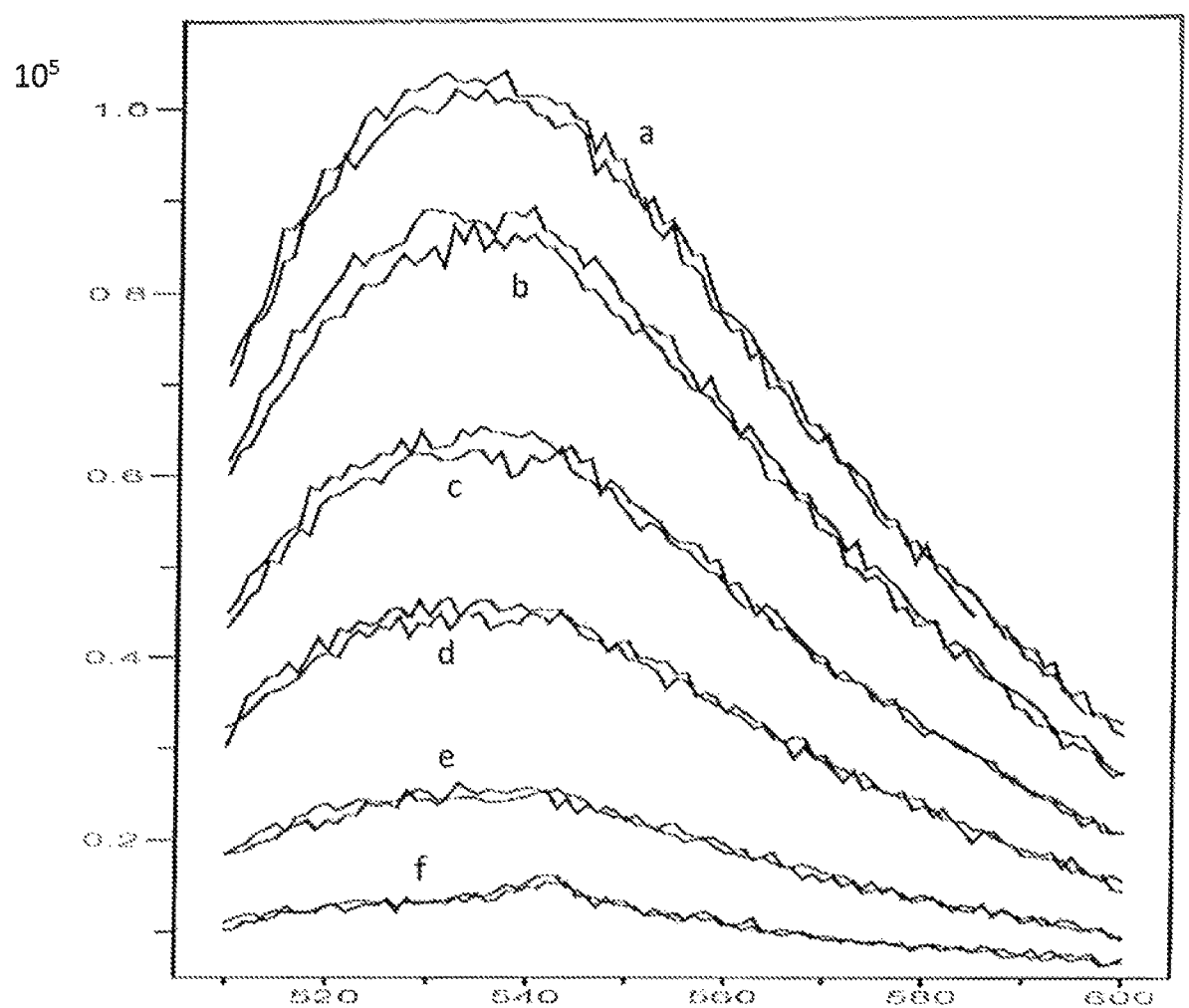
FIG. 4 is a graph showing the results of a sphingosine kinase 1 assay using six different dilutions of the enzyme, where a carrier was used when precipitating the product of the reaction.
Figure 5:
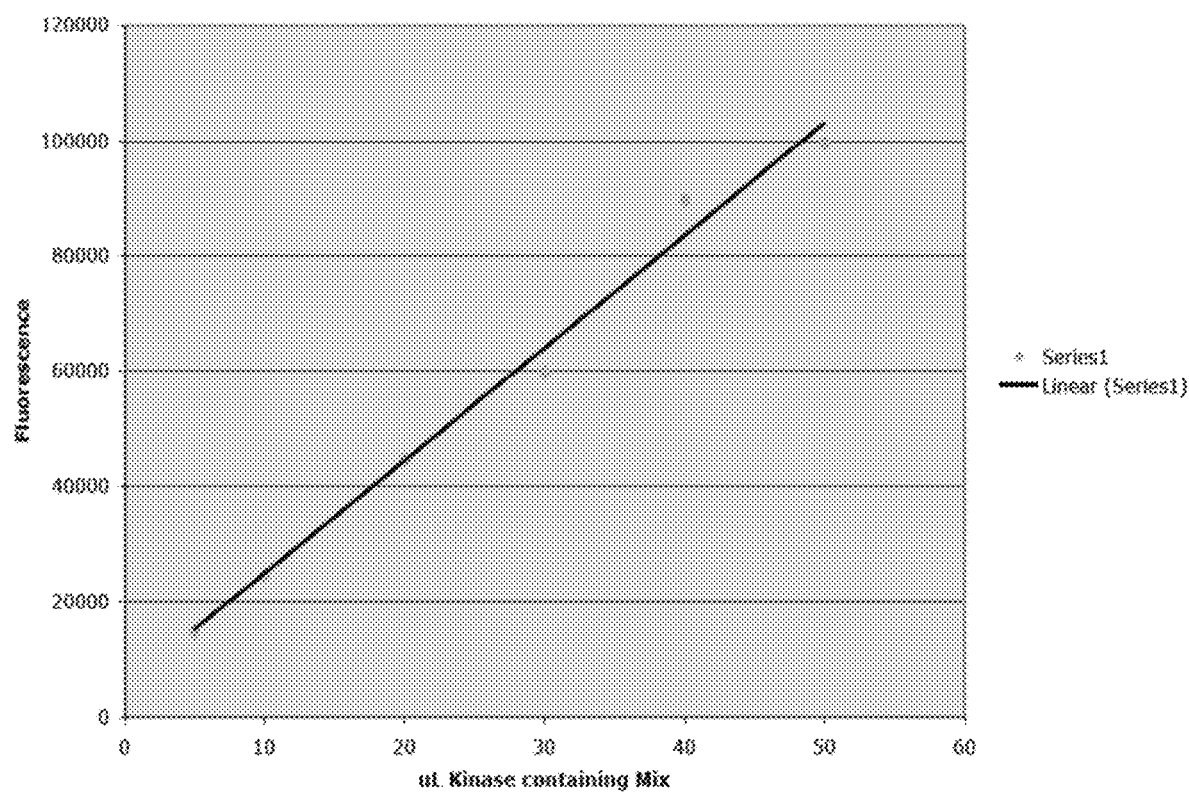
FIG. 5 is a graph of the peak results from each assay where the results are shown in FIG. 4.

FIG. 4 shows the same study except where S1P carrier (without dye) was added at the precipitation step to facilitate precipitation. As shown therein, more precipitation was evident, since the peak fluorescence where only reaction mix with enzyme was used was about 100,000 counts/second (as opposed to about 85,000 counts/sec. when no carrier was used). Thus, in this assay, the addition of carrier resulted in an increase in yield of precipitated fluoresceinated S1P of about 18%. As shown in FIG. 5, the results with carrier were linear.

Figure 6:
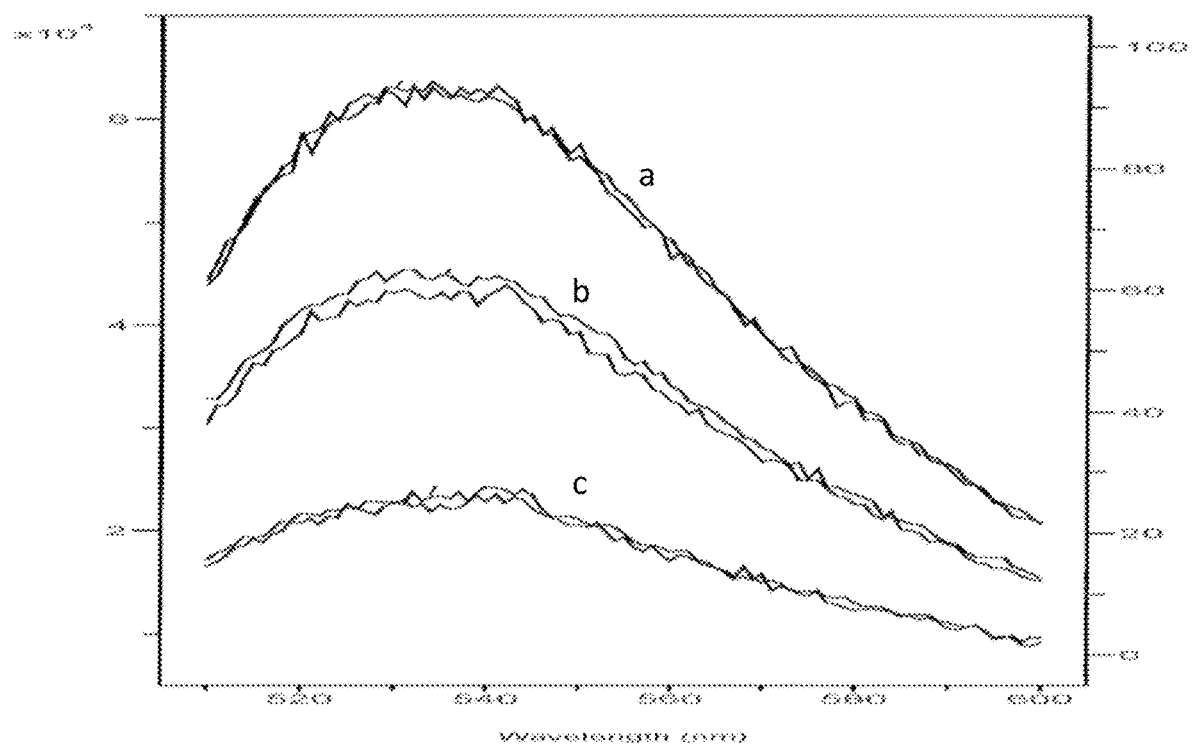
FIG. 6 is a graph showing the results of a sphingosine kinase 1 assay with and without sphingosine kinase 1 inhibitors.

These assays were also utilized to demonstrate inhibition of hSK1 by known SK1 inhibitors. The above reaction mix was prepared and the assay was performed as described above, except 4 µM sphingosine fluoresceine was used, with or without 100 µM of either of two SK1 inhibitors dimethylsphingosine (DMS) and D/L sphingosine. The results are shown in FIG. 6, where the lines labeled "a" are results from two replications of the assay without inhibitors, the lines labeled "b" show results when DMS was added, and the lines labeled "c" show results when D/L sphingosine was added. As shown in FIG. 6, the inclusion of the SK1 inhibitors in the assay mix caused less precipitation of the fluoresceinated product, indicating less fluoresceinated F1P resulting from inhibited enzyme.

Example 2

Detection of Phosphorylated Crosstide Peptide

Example 1 showed that the assay described therein provides linear, quantitative measurements for a phosphorylated small molecule, sphingosine. That result is extended in this example by demonstrating similarly quantitative results for a peptide, Crosstide, with a similar assay. Crosstide is a synthetic oligopeptide (11mer) with the sequence GRPRTSSFAEG (SEQ ID NO:1) (using the common single letter amino acid code), derived from glycogen synthase kinase-3 alpha (GSK-3α). It is phosphorylated at the second serine site (indicated in bold) by several enzymes, including RAC-alpha serine/threonine-protein kinase (AKT1).

Materials and Methods

The following Crosstide reaction mix (1 ml) was prepared:

25 mM Tris HCl pH 8.0
10 mM $MgCl_2$
1.0 mM DTT
45.9 µM crosstide fluoresceine
500 µM ATP
0.01% Triton® X-100
10 µl AKT1 (Sigma Aldrich, St. Louis Mo.)

The same mix was also prepared without the enzyme, as a control and for titration studies, as further described below.

The reaction mix was incubated 1 h at 37° C., then diluted 1:10 in 50 mM Tris-HCl. Following this dilution, a 50 µl aliquot was taken, to which 5 µl of 1 mg/ml crosstide (not fluoresceinated) was added as a carrier (normalizing reagent). Precipitation/wash buffer (200 µl), pH 5.5, consisting of 0.1 M $LaNO_3$, 1.0 M imidazole, 3% Triton® X-100, 0.3 M Tris HCl, and 8 ml concentrated HCl pH 5.5, was added, and the mixture was precipitated on ice for 1 hr.

After precipitation, the mix was transferred to a nylon 0.22 µm filter tube that was first blocked with 6% bactotryptone. The filter tube was centrifuged for 4 minutes at 4000 rpm, and the precipitate was washed twice with 200 µl of the precipitation/wash buffer described above. The precipitate was solubilized and eluted through the filter with 2×100 µl of 20 µM EDTA+50 mM Tris HCl ph 8.0+5% Triton® X-100.

Results and Discussion

Figure 7:
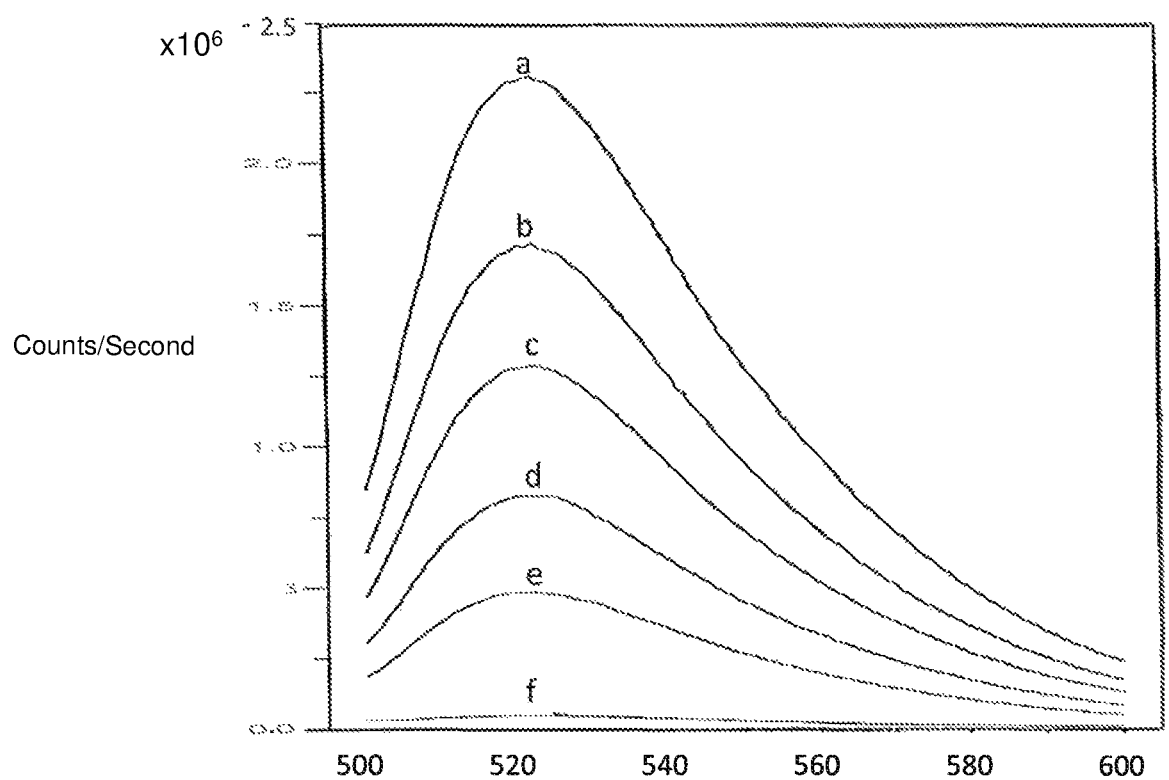
FIG. 7 is a graph showing the results of an AKT1 assay measuring phosphorylated crosstide peptide using six different dilutions of the enzyme.

FIG. 7 shows the results of this assay, where the following 6 mixtures of the reaction mix with and without the AKT1 enzyme were used: the line labeled "a" is the result where 50 µl reaction mix with enzyme was used without adding any reaction mix without enzyme; in "b", 40 µl reaction mix with enzyme and 10 µl reaction mix without enzyme mix was used; in "c", 30 µl reaction mix with enzyme and 20 µl reaction mix without enzyme was used; in "d" 20 µl reaction mix with enzyme and 30 µl reaction mix without enzyme was used; in "e" 10 µl reaction mix with enzyme and 40 µl reaction mix without enzyme was used; in "f" 0 µl reaction mix with enzyme and 50 µl reaction mix without enzyme was used.

Figure 8:
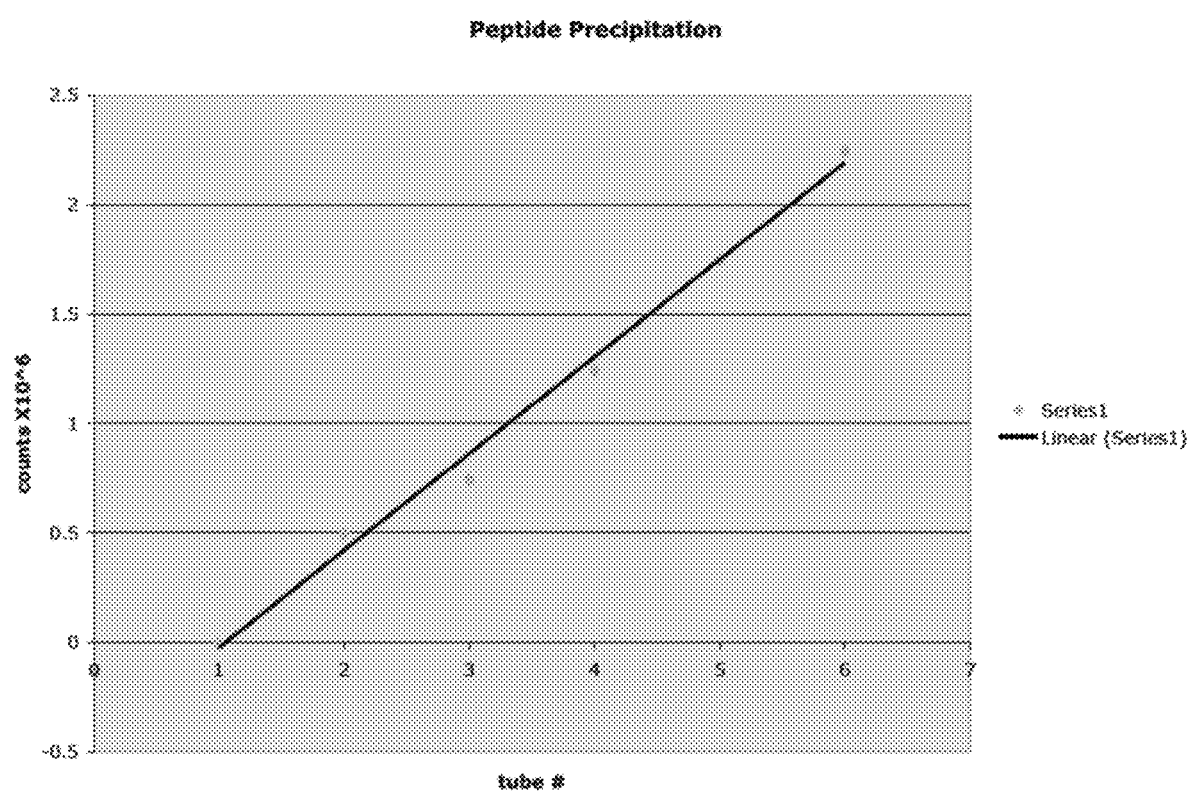
FIG. 8 is a graph of the peak results from each assay where the results are shown in FIG. 7.

A graph of the peak results from these assays is shown in FIG. 8. The assay shows linear results, indicating quantitative precipitation of the fluoresceinated Crosstide.

Example 3

Precipitation of Sulfated Peptide

Examples 1 and 2 describe assays where a dye-conjugated small molecule (Example 1) and a peptide (Example 2) is phosphorylated and quantitatively separated from the unphosphorylated substrate by precipitation, using a metal ion. Because a phosphate functional group is a divalent anion, those Examples do not indicate whether a compound with a monovalent anion functional group, such as a sulfate group, could be precipitated. This Example addresses that question, and establishes that such a compound can indeed be precipitated, thus establishing that a compound with a monovalent functional group can be separated by the methods provided herein.

The following sulfated peptide ("EBJR") was prepared by AnaSpec, Inc. (San Jose, Calif.) (using the common single letter amino acid code; 5FAM=5-Carboxyfluorescein): 5FAM-GPWLEEEEEAY*GWMDF (SEQ ID NO:2). The tyrosine residue (Y*) was sulfated.

The following quantities of EBJR was prepared in 50 µl of 50 mM Tris buffer, pH 8.0:

Mole EBJR
$5.93 \times 10^{-12}$
$2.97 \times 10^{-11}$
$5.93 \times 10^{-11}$
$5.93 \times 10^{-10}$
$3.00 \times 10^{-9}$
$6.00 \times 10^{-9}$ To these EBJR preparations, either 1 µl of 1M phenol phosphate or 2 µl 10 mM sodium sulfate was added as a carrier, along with 10 µl of 1 M barium acetate, 200 µl of 50 mM Tris, pH 8.0, and 5 µl of 600 mM HCl. The final pH of this solution was about 6.0. This mixture was precipitated on ice for 1 hr.

After precipitation, the mix was transferred to a nylon 0.22 µm filter tube that was first blocked with 6% bactotryptone. The filter tube was centrifuged for 4 minutes at 10,000 rpm, and the precipitate (retained on the filter) was washed with 200 µl of a wash buffer consisting of 100 mM barium acetate in 50 mM Tris, pH 8.0. The precipitate was solubilized and eluted through the filter with 2×100 µl of an elution buffer consisting of 20 µM EDTA+50 mM Tris HCl ph 8.0+5% Triton® X-100.

Figure 9:
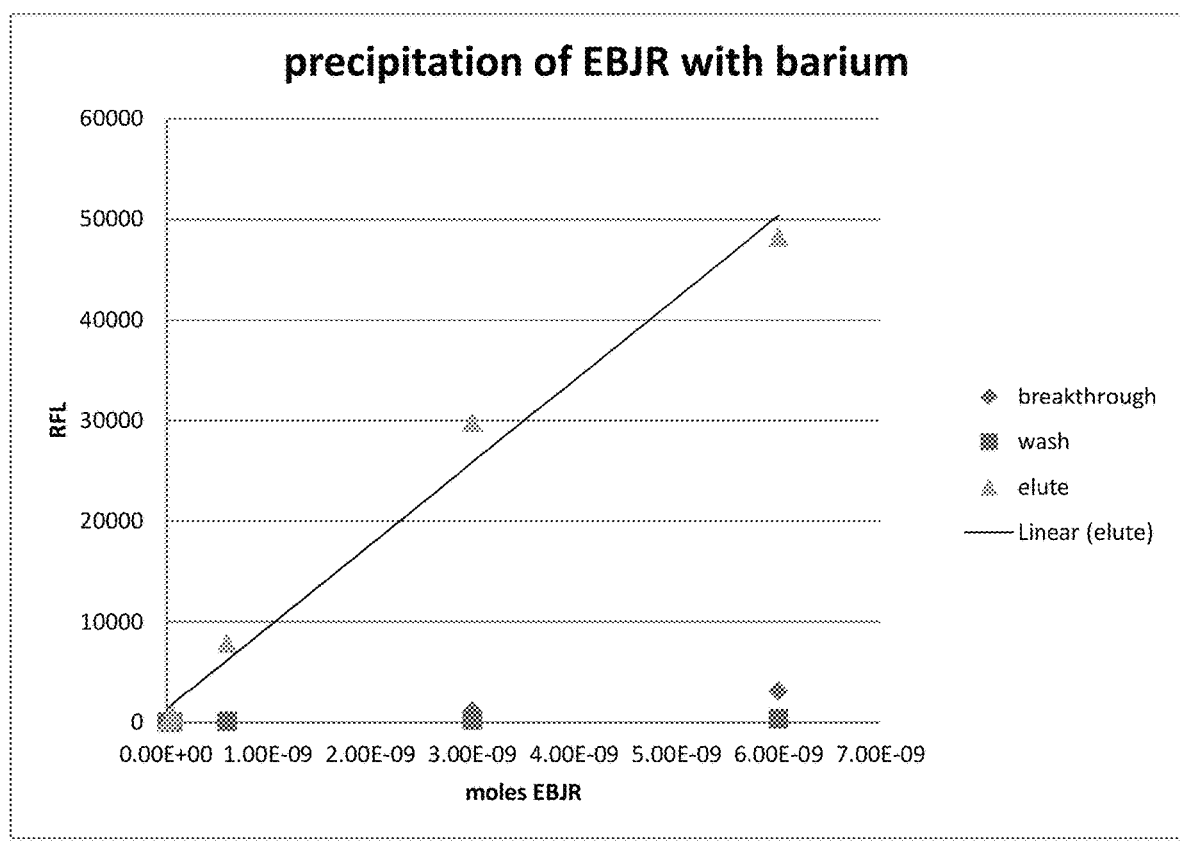
FIG. 9 is a graph showing the results of a precipitation of various concentrations of fluoresceinated, sulfated EBJR peptide.

FIG. 9 shows the results of the precipitation of fluoresceinated, sulfated EBJR, where the sodium sulfate carrier was used. The precipitation and elution of increasing concentrations of the sulfated peptide was linear, with minimal peptide passing through the filter as breakthrough or in the washes, showing essentially complete precipitation of the peptide. Results using the phenol phosphate carrier were very similar to the results with the sodium sulfate carrier shown in FIG. 9.

These results demonstrate that compounds with monovalent anions can be precipitated quantitatively.

In view of the above, it will be seen that the several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method for detecting or quantifying an activity in a sample that causes a compound to gain a functional group, the method comprising the steps of:
   (a) providing:
      (i) a compound which can gain a functional group, the compound comprising at least one non-radioactive signaling moiety;
      (ii) a chemical source of the functional group which can be gained by the compound; and
      (iii) a sample;
   wherein the compound is a lipid, and
   wherein the functional group is a glycosyl group;
   (b) forming a mixture comprising the compound, the source of the functional group and the sample, and incubating the mixture under conditions suitable for the compound to gain the functional group; and (c) capturing any compound that has gained the functional group on a matrix comprising a glycosyl group-binding lectin and separating said compound which has gained the functional group from any compound which has not gained the functional group; and (d) detecting or quantifying the non-radioactive signaling moiety of any captured separated compounds having the functional group, thereby detecting or quantifying the activity in the sample.

2. The method of claim 1, wherein the non-radioactive signaling moiety comprises a fluorescent compound, a phosphorescent compound, a chemiluminescent compound, a chromogenic compound, a chelating compound, an electron dense compound, a magnetic compound, an energy transfer member or pair, an intercalating compound, an antibody, an antigen, a hapten, a receptor, a hormone, a ligand or an enzyme, or any combination thereof.

3. A method for detecting or quantifying an activity in sample which removes a functional group from a compound, the method comprising the steps of:

(a) providing:
(i) a compound comprising a functional group and at least one non-radioactive signaling moiety; and
(ii) a sample;

wherein the compound is a lipid, and wherein the functional group is a glycosyl group;

(b) forming a mixture comprising the compound and the sample and incubating the mixture under conditions suitable for the compound to lose the functional group; and (c) capturing on a matrix comprising a glycosyl group-binding lectin and separating any compound that has the functional group following the incubation from any compound which has lost the functional group; and (d) detecting or quantifying the non-radioactive signaling moiety of any captured separated compounds having the functional group, thereby detecting or quantifying the activity in the sample.

4. The method of claim 3, wherein the non-radioactive signaling moiety comprises a fluorescent compound, a phosphorescent compound, a chemiluminescent compound, a chromogenic compound, a chelating compound, an electron dense compound, a magnetic compound, an energy transfer member or pair, an intercalating compound, an antibody, an antigen, a hapten, a receptor, a hormone, a ligand or an enzyme, or any combination thereof.

* * * * *